(12) United States Patent
Okada et al.

(10) Patent No.: US 8,963,070 B2
(45) Date of Patent: Feb. 24, 2015

(54) METHOD FOR MEASURING CARBON CONCENTRATION IN POLYCRYSTALLINE SILICON

(75) Inventors: Junichi Okada, Niigata (JP); Kouichi Kobayashi, Niigata (JP); Fumitaka Kume, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/110,013

(22) PCT Filed: Apr. 3, 2012

(86) PCT No.: PCT/JP2012/002313
§ 371 (c)(1),
(2), (4) Date: Oct. 4, 2013

(87) PCT Pub. No.: WO2012/137480
PCT Pub. Date: Oct. 11, 2012

(65) Prior Publication Data
US 2014/0021344 A1 Jan. 23, 2014

(30) Foreign Application Priority Data
Apr. 4, 2011 (JP) .................................. 2011-082983

(51) Int. Cl.
*G01D 18/00* (2006.01)
*G12B 13/00* (2006.01)
(Continued)

(52) U.S. Cl.
CPC ............... *G01J 3/42* (2013.01); *G01N 21/3563* (2013.01); *G01N 21/274* (2013.01)
USPC ..................................................... 250/252.1

(58) Field of Classification Search
USPC ........................................................ 250/252.1
See application file for complete search history.

(56) References Cited

U.S. PATENT DOCUMENTS

| 5,444,246 A | 8/1995 | Kitagawara et al. |
| 5,808,745 A | 9/1998 | Shirai et al. |
| 2005/0211901 A1 | 9/2005 | Crossmann et al. |
| 2007/0238189 A1 | 10/2007 | Kreszowski |

FOREIGN PATENT DOCUMENTS

| CN | 201444141 U | 4/2010 |
| JP | 4 310513 | 11/1992 |

(Continued)

OTHER PUBLICATIONS

ASTM F1723-02: "Standard Practice for Evaluation of Polycrystalline Silicon Rods by Float-Zone Crystal Growth and Spectroscopy", (Total 9 Pages), (Mar. 2002).

(Continued)

*Primary Examiner* — David Porta
*Assistant Examiner* — Abra Fein
(74) *Attorney, Agent, or Firm* — Oblon, Spivak, McClelland, Maier & Neustadt, L.L.P.

(57) ABSTRACT

The present invention provides a method for making it possible to easily and simply measure approximate concentration of substitutional carbon impurities in a desired position in a polycrystalline silicon rod. A polycrystalline silicon plate is sliced out from a polycrystalline silicon rod and both surfaces of the polycrystalline silicon plate are mirror-polished to reduce the polycrystalline silicon plate to thickness of 2.12±0.01 mm. A calibration curve is created according to an infrared absorption spectroscopy and on the basis of a standard measurement method using a single crystal silicon standard sample having known substitutional carbon concentration and thickness of 2.00±0.01 mm, an infrared absorption spectrum in a frequency domain including an absorption zone peak of substitutional carbon of the polycrystalline silicon plate after the mirror polishing is calculated under conditions same as conditions during the calibration curve creation, and substitutional carbon concentration is calculated without performing thickness correction.

2 Claims, 4 Drawing Sheets

(51) Int. Cl.
*G01J 3/42* (2006.01)
*G01N 21/3563* (2014.01)
*G01N 21/27* (2006.01)

(56) References Cited

FOREIGN PATENT DOCUMENTS

| | | |
|---|---|---|
| JP | 5 26803 | 2/1993 |
| JP | 6 194310 | 7/1994 |
| JP | 7 297247 | 11/1995 |
| JP | 8 105716 | 4/1996 |
| JP | 3178607 B2 | 4/2001 |
| JP | 2007 279042 | 10/2007 |
| KR | 10-0157030 B1 | 7/1998 |

OTHER PUBLICATIONS

ASTM F1391-93: "Standard Test Method for Substitutional Atomic Carbon Content of Silicon by Infrared Absorption", Japan Electronics and Information Technology Industries Association, (Total 6 pages), (2000).
F. Shimura "Semiconductor Silicon Crystal Technology", Academic Press, Inc., pp. 148-151, (1989).
"Standard Measurement Method for Substitutional Carbon Atom concentration in Silicon Crystal by Infrared Absorption", Japan electronics and Information Technology Industries Standard (JEITA EM-3503), (Total 18 pages), (Mar. 1998).
International Search Report Issued May 29, 2012 in PCT/JP12/002313 Filed Apr. 3, 2012.
Notice of Allowance dated Sep. 17, 2014 issued in corresponding Korean patent application No. 10-2013-7026140.
European Search Report dated Nov. 19, 2014, issued in corresponding European patent application No. 12767547.8.
Hwang et al. "Measurement of Carbon Concentration in Polycrystalline Silicon Using FTIR", J. Electrochem. Soc., vol. 138, No. 2, Feb. 1991, pp. 576-581.
Chinese Office Action dated Oct. 22, 2014 issued in corresponding Chinese patent application No. 201280016408.7.

METHOD FOR MEASURING CARBON CONCENTRATION IN POLYCRYSTALLINE SILICON

TECHNICAL FIELD

The present invention relates to a method for measuring carbon concentration in polycrystalline silicon.

BACKGROUND ART

As a substrate for a semiconductor device or a solar battery, in general, a silicon substrate is used. As a material of such a silicon substrate, polycrystalline silicon manufactured by a Siemens method is used. However, as requirements for high integration and high quality of a final product become stricter, a high purity requirement for the polycrystalline silicon is also becoming stricter.

As light element impurities in silicon crystal, interstitial oxygen and substitutional carbon are known. The interstitial oxygen is an impurity that precipitates in crystal and causes dislocation and stacking fault. The substitutional carbon is an impurity that facilitates the precipitation of the oxygen. Concentration measuring methods for the interstitial oxygen and the substitutional carbon have been examined for a long time. For single crystal silicon, a standard measurement method employing Fourier-transform infrared spectroscopy has been established by agencies such as ASTM and JEIDA.

Incidentally, a large number of graphite members are used in a reactor used in precipitating polycrystalline silicon. Therefore, carbon generated from the graphite members tends to be taken into the polycrystalline silicon. Since such carbon impurities result in being taken into single crystal silicon manufactured from the polycrystalline silicon unless special removal of the carbon impurities is performed, improvement of purity of the single crystal silicon is hindered. Therefore, in order to realize low carbon concentration of the substrate for the semiconductor device or the solar battery, it is necessary to manage the carbon concentration of the polycrystalline silicon from which the substrate is manufactured.

Therefore, methods for evaluating carbon concentration in polycrystalline silicon have been examined and standardized. For example, one of ASTM standards (Non-Patent Literature 1) specifies a method for measuring carbon concentration in polycrystalline silicon according to a combination of a floating zone (FZ) method and an optical method (an infrared spectroscopy or a photoluminescence method).

In this method, first, a hole is drilled in a polycrystalline silicon rod obtained by being precipitated on a silicon core wire and a cylinder (a core) having a diameter of about 20 mm is pulled out. Subsequently, in order to eliminate damage caused on the core surface when the core is sliced out, the core surface is etched 100 µm or more by $HNO_3$/HF mixed acid. A single crystal silicon rod is obtained by the FZ method using the core. For example, carbon concentration measurement is performed by the infrared spectroscopy conforming to Non-Patent Literature 2.

However, in the case of this method, because an effective segregation coefficient of carbon impurities in silicon crystal is small ($k_{eff}$=0.07: see Non-Patent Literature 3), there is a problem in that, if a single crystal rod grown by the FZ method is short, accurately measurement of carbon concentration in material polycrystalline silicon is difficult. More specifically, in the case of impurities having an effective segregation coefficient smaller than 1, the impurities included in the material polycrystalline silicon are concentrated on the material side because the impurities tend to be taken into an FZ melting region. Therefore, when it is attempted to accurately measure the carbon concentration of the material polycrystalline silicon, it is necessary to grow a long FZ single crystal rod.

Japanese Patent Application Laid-Open Publication No. 2007-279042 (Patent Literature 1) discloses a measuring method that makes use of the fact that carbon concentration in a freezing and melting region is higher than carbon concentration in a polycrystalline silicon composition. In this method, a polycrystalline silicon core extracted from the polycrystalline silicon composition is FZ-grown by an FZ crystal growing device to obtain a core including a single crystal region and a freezing and melting region. The core is annealed for at least two hours at temperature in a range of 1150° C. to 1360° C. Samples extracted from each of the single crystal region and the freezing and melting region are subjected to an infrared spectroscopic analysis to create a calibration curve and calculate the carbon concentration of the single crystal region. The carbon concentration of the polycrystalline silicon composition is determined based on the carbon concentration of the single crystal region.

CITATION LIST

Patent Literature

Patent Literature 1: Japanese Patent Application Laid-Open Publication No. 2007-279042

Non-Patent Literature

Non-Patent Literature 1: ASTM F1723-02: "Standard Practice for Evaluation of Polycrystalline Silicon Rods by Float-Zone Crystal Growth and Spectroscopy"
Non-Patent Literature 2: ASTM F1391-93: "Standard Test Method for Substitutional Atomic Carbon Content of Silicon by Infrared Absorption"
Non-Patent Literature 3: F. Shimura "Semiconductor Silicon Crystal Technology" Academic Press, Inc. (1989) p. 148 to 151
Non-Patent Literature 4: Japan Electronics and Information Technology Industries Standard (JEITA EM-3503) "Standard Measurement Method for Substitutional Carbon Atom Concentration in Silicon Crystal by Infrared Absorption"

SUMMARY OF INVENTION

Technical Problem

However, as explained above, the conventional method requires a process for sample production by the FZ method. In addition, in the method described in Non-Patent Literature 1, it is necessary to use a long FZ single crystal rod in order to accurately measure the concentration of carbon having a small effective segregation coefficient in silicon crystal. The method described in Patent Literature 1 not only is extremely complicated but also requires annealing at high temperature.

The present invention has been devised in view of the problems of the conventional methods explained above and an object of the present invention is to provide a method for making it possible to simply and easily measure, in a short time, the concentration of a substitutional carbon impurity in a desired position of a polycrystalline silicon rod.

Solution to Problem

In order to solve the problems, a method for measuring carbon concentration in polycrystalline silicon according to a first aspect of the present invention is characterized by including: slicing out a polycrystalline silicon plate from a polycrystalline silicon rod; mirror-polishing both surfaces of the polycrystalline silicon plate to reduce the polycrystalline silicon plate to thickness of 2.12±0.01 mm; creating a calibration curve according to an infrared absorption spectroscopy and on the basis of a standard measurement method using a single crystal silicon standard sample having known substitutional carbon concentration and thickness of 2.00±0.01 mm; calculating, under conditions same as conditions during the calibration curve creation, an infrared absorption spectrum in a frequency domain including an absorption zone peak of substitutional carbon in a desired place of the polycrystalline silicon plate after the mirror polishing; and calculating substitutional carbon concentration of the polycrystalline silicon plate on the basis of the calibration curve without performing thickness correction.

A method of measuring carbon concentration in polycrystalline silicon according to a second aspect of the present invention is characterized by including: slicing out at least two adjacent polycrystalline silicon plates having different thicknesses from a polycrystalline silicon rod; mirror-polishing both surfaces of each of the polycrystalline silicon plates to prepare a first polycrystalline silicon plate thinner than 2.12 mm and a second polycrystalline silicon plate thicker than 2.12 mm; creating a first calibration curve according to an infrared absorption spectroscopy and on the basis of a standard measurement method using a single crystal silicon standard sample having known substitutional carbon concentration and thickness of 2.00±0.01 mm; calculating, under conditions same as conditions during the first calibration curve creation, an infrared absorption spectrum in a frequency domain including an absorption zone peak of substitutional carbon in a desired place of the first and second polycrystalline silicon plates after the mirror polishing; calculating substitutional carbon concentration of the first and second polycrystalline silicon plates on the basis of the first calibration curve without performing thickness correction; creating a second calibration curve from the substitutional carbon concentrations and the thicknesses of the first and second polycrystalline silicon plates; and setting carbon concentration corresponding to the thickness 2.00±0.01 mm of the second calibration curve as carbon concentration of a sliced-out region of the polycrystalline silicon plate.

Advantageous Effects of Invention

According to the present invention, it is possible to perform an approximate concentration measurement of substitutional carbon without applying single crystallization by the FZ method or the like and without performing special pre-heat treatment. That is, according to the present invention, there is provided a method for making it possible to easily and simply measure approximate concentration of substitutional carbon impurities in a desired position in a polycrystalline silicon rod.

DESCRIPTION OF EMBODIMENTS

Figure 1:
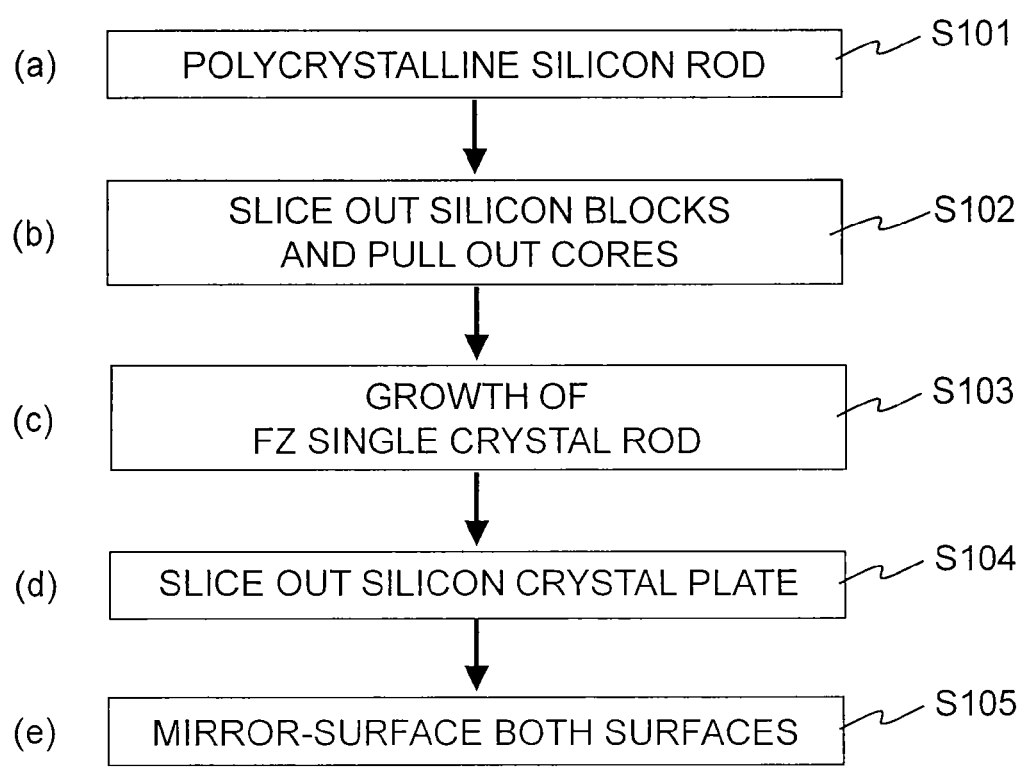
FIG. 1 is a diagram showing an example of a preparation process for a sample for carbon concentration measurement.

A method of measuring carbon concentration in polycrystalline silicon in the present invention is explained below with reference to the drawing.

A peak of infrared absorption by substitutional carbon in silicon crystal is found at 605 cm$^{-1}$. A standard measurement method of using single crystal silicon is specified by the Japan Electronics and Information Technology Industries Association (JEITA) (see Non-Patent Literature 4). However, since a method of measuring substitutional carbon in polycrystalline silicon including crystal grains is not standardized, if it is attempted to calculate carbon concentration on the basis of the standard measurement method, it is necessary to once single-crystallize the polycrystalline silicon. Therefore, it is an object of the present invention to easily, simply, and quickly measure approximate concentration of substitutional carbon impurities in a desired position in a polycrystalline silicon rod according to an infrared absorption method without performing such a complicated procedure.

As a prerequisite for attaining the object, the inventors checked a relation between carbon concentration in single crystal silicon calculated by the standard measurement method and carbon concentration obtained by measuring polycrystalline silicon having carbon concentration substantially the same as the carbon concentration of the single crystal silicon.

Preparation of a sample for carbon concentration measurement: FIG. 1 is a diagram showing an example of a preparation process for a sample for carbon concentration measurement. First, six polycrystalline silicon rods vapor-phase grown by the Siemens method were prepared (S101). For each of the polycrystalline silicon rods, cores (silicon blocks) having length of 150 mm and a diameter of 20 mm were pulled out in a cylindrical shape from the longitudinal direction (S102). In the following explanation, these cores are referred to as cores 1 to 6. Subsequently, an FZ single crystal rod having a diameter of about 10 mm and length of about 200 mm was grown from each of the cores 1 to 6 (S103).

Figure 2:
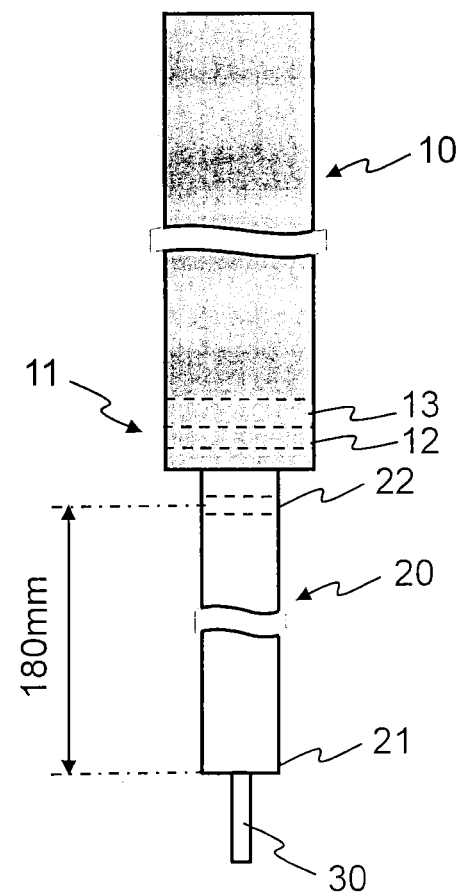
FIG. 2 is a diagram for explaining slicing-out of a silicon crystal plate from an FZ single crystal rod and a gripped portion.

FIG. 2 is a diagram for explaining slicing-out of a silicon crystal plate from an FZ single crystal rod and a gripped portion. In the figure, reference numeral 10 denotes a core (a silicon block), reference numeral 20 denotes an FZ single crystal rod, and reference numeral 30 denotes a seed. As shown in the figure, one disc-like FZ crystal (22) was sliced out at thickness of about 2 mm from a position at about 180 mm from a cone portion (21) of each of FZ single crystal rods. One each of polycrystalline silicon plates (12, 13) having thickness of about 2 mm (thickness A) and about 2.5 mm (thickness B) were sliced out from an FZ single crystal rod near region (11) of a portion gripped during FZ single crystal rod growth (S104).

Both surfaces of the single crystal silicon plate (22) sliced out from each of the FZ single crystal rod were mirror-surfaced to adjust the thickness thereof to be within a range of 2.00±0.01 mm. Similarly, both surfaces of the polycrystalline silicon plates (12, 13) sliced out from the gripped portion of each of the cores were mirror-surfaced and thicknesses thereof were measured by a dial gauge having a minimum scale of 1 μm (0.001 mm) (S105).

Carbon concentration measurement: Transmission spectra in a frequency range of 500 cm$^{-1}$ to 700 cm$^{-1}$ of one FZ single crystal silicon plate and two polycrystalline silicon plates prepared by the procedure from each of the six cores were measured by an infrared spectrometer. Therefore, carbon concentration measurement targets were six FZ single crystal silicon plates and twelve polycrystalline silicon plates.

Measurement conditions were based on the Japan Electronics and Information Technology Industries Standard (JEITA EM-3503: Non-Patent Literature 4) described above. Note that, as a reference sample, only one single crystal silicon plate sliced out from a cone portion of an FZ single crystal rod, which is a region not substantially including carbon, and machined into mirror surfaces on both surfaces to have thickness in a range of 2.00±0.01 mm was prepared and used. Carbon concentration was measured using a Fourier-transform infrared spectroscopic instrument at resolution of 2 $cm^{-2}$ with a cumulative number set to 400 times. Note that a beam splitter is Ge/KBr, a detector is DTGS, and a light source is a Globar lamp.

Figure 3:
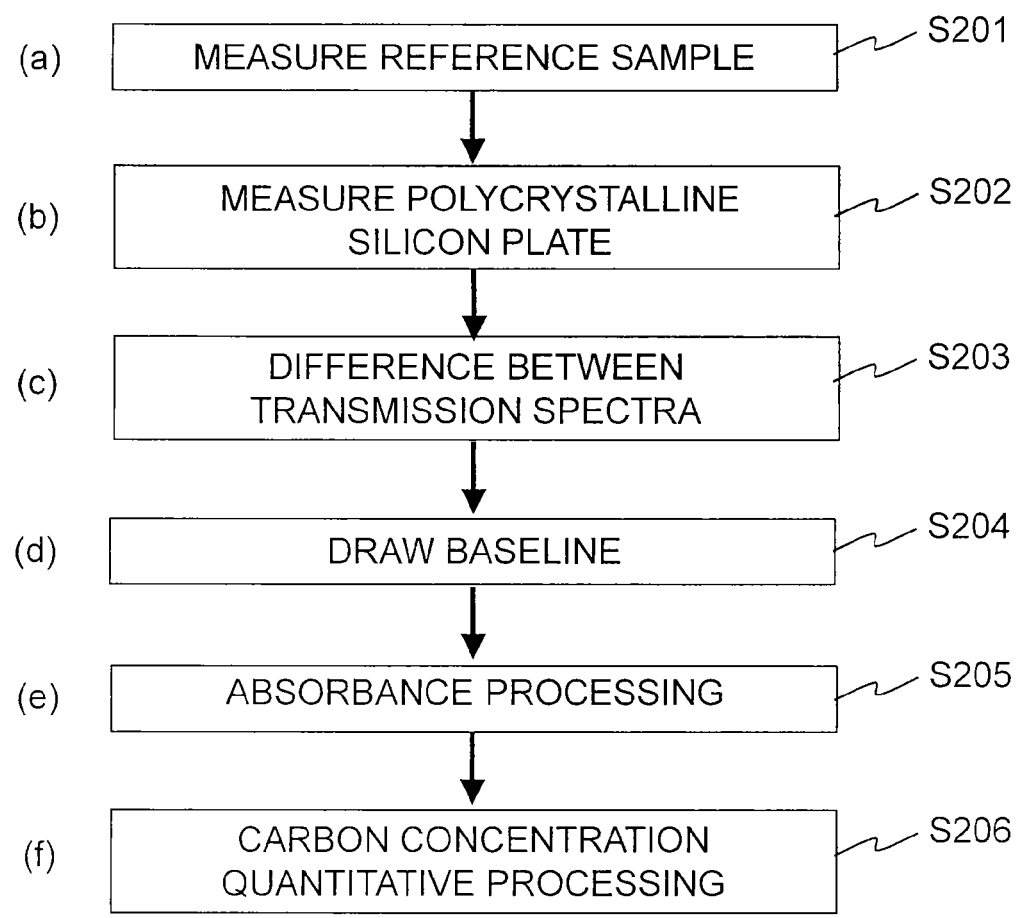
FIG. 3 is a diagram for explaining an example of a process of carbon concentration measurement.

FIG. 3 is a diagram for explaining an example of a process of carbon concentration measurement. First, a transmission spectrum of the reference sample was measured (S201). Subsequently, transmission spectra of the six FZ single crystal silicon plates and the twelve polycrystalline silicon plates were measured (S202).

After the measurement of the spectra, a difference between the transmission spectrum of the reference sample and the transmission spectrum of each of the FZ single crystal silicon plates was calculated (S203). A baseline extending across both sides of a carbon peak (604 $cm^{-1}$) of the difference spectrum was drawn (S204). Absorbance was calculated from the baseline and the peak (S205). Substitutional carbon concentrations of the respective FZ single crystal silicon plates were calculated according to correction of the sample thickness (S206). Consequently, a calibration curve was obtained.

Similarly, a difference between the transmission spectrum of the reference sample and the transmission spectrum of each of the polycrystalline silicon plates was calculated. Substitutional carbon concentrations of the respective polycrystalline silicon plates were calculated according to correction of the sample thickness from absorbance calculated by drawing a baseline extending across both sides of a carbon peak (604 $cm^{-1}$) of the difference spectrum. A result of the calculation is shown in Table 1. Note that a unit of thickness is mm and a unit of concentration is ppma. In the table, concentration A indicates a carbon concentration calculation value of a polycrystalline silicon plate having thickness A and concentration B indicates a carbon concentration calculation value of a polycrystalline silicon plate having thickness B.

As summarized in the table, whereas all carbon concentrations of the respective FZ single crystal silicon plates indicate positive values, carbon concentrations of negative values are obtained from all the polycrystalline silicon plates having the thickness A. Carbon concentration cannot be negative. Therefore, the above result indicates that meaningful values are not obtained even if the carbon concentration of polycrystalline silicon is measured by the standard measurement method for single crystal silicon.

Therefore, for each of the cores, a calibration curve was created using the carbon concentration obtained from the polycrystalline silicon plate having the thickness A and the carbon concentration obtained from the polycrystalline silicon plate having the thickness B. Thickness at which the a value and carbon concentration of the FZ single crystal silicon plate obtained from the core generally coincide with the calibration curve is calculated as thickness C. Concentration C shown in Table 1 is carbon concentration read at the point of the sample thickness C from the calibration curve.

Figure 4:
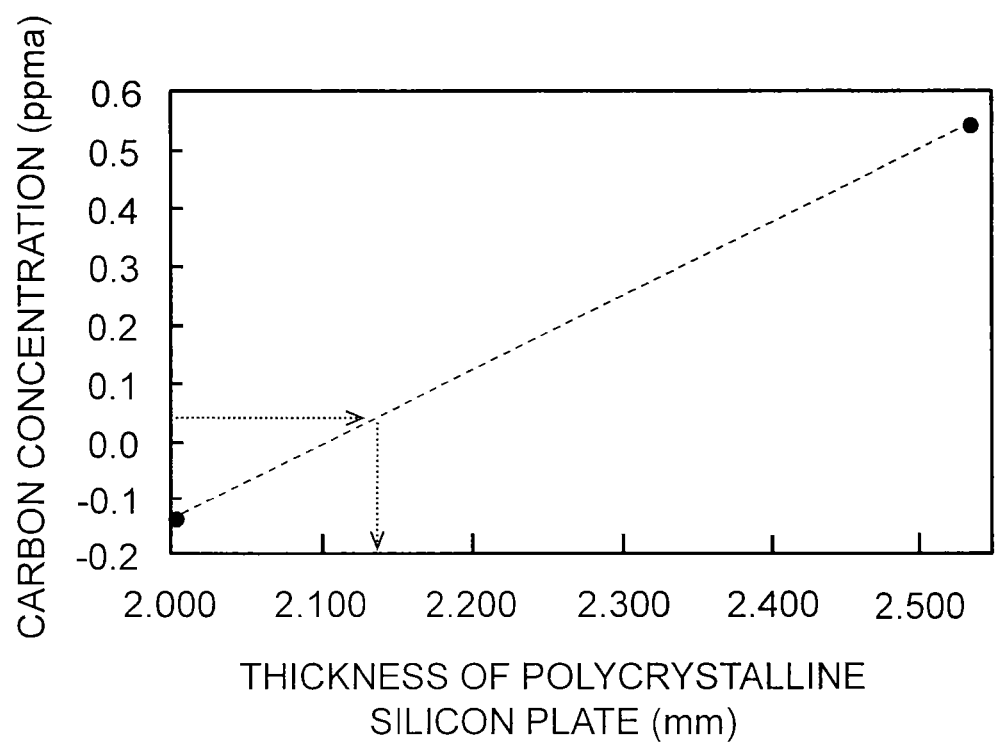
FIG. 4 is a diagram showing polycrystalline silicon plate thickness dependency of substitutional carbon concentration.

FIG. 4 is a diagram showing polycrystalline silicon plate thickness dependency of substitutional carbon concentration. A result shown in FIG. 4 is a calibration curve for the core 1. In this case, carbon concentration of the FZ single crystal silicon plate obtained from the core 1 is 0.03742 ppma. Therefore, thickness for giving this carbon concentration value in the calibration curve is 2.135 mm. This thickness is the thickness C.

That is, if the carbon concentration of the polycrystalline silicon plate having the thickness C is measured on the basis of the standard measurement method, it is possible to perform accurate concentration measurement of substitutional carbon in polycrystalline silicon without applying single crystallization by the FZ method or the like and without performing special pre-heat treatment.

An average value of the thickness C shown in Table 1 is 2.12 mm. Therefore, if the thickness of a polycrystalline silicon plate is set to 2.12 mm and carbon concentration measurement is performed on the basis of the standard measurement method, it is possible to easily and simply measure approximate concentration of substitutional carbon impurities in a desired position in a polycrystalline silicon rod. Note that, since an error of sample thickness is specified as ±0.01 mm in the standard measurement method of JEITA, the above 2.12 mm should substantially be represented as 2.12±0.01 mm.

That is, in the present invention, carbon concentration in polycrystalline silicon is measure by slicing out a polycrystalline silicon plate from a polycrystalline silicon rod, mirror-polishing both surfaces of the polycrystalline silicon plate to reduce the polycrystalline silicon plate to thickness of 2.12±0.01 mm, creating a calibration curve according to an infrared absorption spectroscopy and on the basis of the standard measurement method using a single crystal silicon standard sample having known substitutional carbon concentration and thickness of 2.00±0.01 mm, calculating, under conditions same as conditions during the calibration curve creation, an infrared absorption spectrum in a frequency domain including an absorption zone peak of substitutional carbon in a desired place of the polycrystalline silicon plate

TABLE 1

| Sample | FZ single crystal Si | | Polycrystalline Si | | | | | |
| --- | --- | --- | --- | --- | --- | --- | --- | --- |
| | Thickness | Concentration | Thickness A | Concentration A | Thickness B | Concentration B | Thickness C | Concentration C |
| Core 1 | 2.000 | 0.03742 | 2.001 | −0.13153 | 2.529 | 0.53496 | 2.135 | 0.03742 |
| Core 2 | 2.000 | 0.04534 | 2.068 | −0.02053 | 2.521 | 0.61345 | 2.115 | 0.04534 |
| Core 3 | 2.000 | 0.01281 | 2.043 | −0.06662 | 2.522 | 0.58329 | 2.102 | 0.01281 |
| Core 4 | 2.000 | 0.03016 | 2.010 | −0.06138 | 2.442 | 0.51610 | 2.079 | 0.03016 |
| Core 5 | 2.000 | 0.04823 | 1.845 | −0.34985 | 2.385 | 0.34177 | 2.156 | 0.04823 |
| Core 6 | 2.000 | 0.01770 | 1.874 | −0.35804 | 2.356 | 0.29423 | 2.152 | 0.01770 | after the mirror polishing, and calculating substitutional carbon concentration of the polycrystalline silicon plate on the basis of the calibration curve without performing thickness correction. The single crystal silicon standard sample having the known substitutional carbon concentration is desirably created in proportion to a standard sample used in a round robin or the like by the former Japan Electronic Industry Development Association (JEIDA).

Note that, in order to obtain a value closer to true carbon concentration, as explained above, it is desirable to slice out at least two adjacent polycrystalline silicon plates having different thicknesses from a polycrystalline silicon rod, mirror-polish both surfaces of each of the polycrystalline silicon plates to prepare a first polycrystalline silicon plate thinner than 2.12 mm and a second polycrystalline silicon plate thicker than 2.12 mm, create a first calibration curve according to the infrared absorption spectroscopy and on the basis of the standard measurement method using a single crystal silicon standard sample having known substitutional carbon concentration and thickness of 2.00±0.01 mm, calculate, under conditions same as conditions during the first calibration curve creation, an infrared absorption spectrum in a frequency domain including an absorption zone peak of substitutional carbon in a desired place of the first and second polycrystalline silicon plates after the mirror polishing, calculate substitutional carbon concentration of the first and second polycrystalline silicon plates on the basis of the first calibration curve without performing thickness correction, then, further create a second calibration curve from the substitutional carbon concentrations and the thicknesses of the first and second polycrystalline silicon plates, and set carbon concentration corresponding to the thickness 2.00±0.01 mm of the second calibration curve as carbon concentration of a sliced-out region of the polycrystalline silicon plate.

The second calibration curve explained above makes it possible to more accurately calculate the carbon concentration of the sliced-out region of the polycrystalline silicon plate. Therefore, it is possible to obtain a more accurate value compared with a value calculated from a single calibration curve.

Example: one FZ single crystal silicon plate having thickness of 2.000 mm and one polycrystalline silicon plate having thickness of 2.006 mm and one polycrystalline silicon plate having thickness of 2.477 mm were prepared from a polycrystalline silicon rod both the surfaces thereof were polished to mirror surfaces.

For these samples, transmission spectra were measured and carbon concentrations of the respective samples were calculated. Then, the carbon concentration of the FZ single crystal silicon plate was 0.08758 ppma and the carbon concentration of the polycrystalline silicon plate having the thickness of 2.006 mm and the carbon of the polycrystalline silicon plate having the thickness of 2.477 mm were respectively −0.06909 ppma and 0.56866 ppma.

A second calibration curve was created from the carbon concentration value −0.06909 ppma of the polycrystalline silicon plate having the thickness of 2.006 mm and the carbon concentration value 0.56866 ppma of the polycrystalline silicon plate having the thickness of 2.477 mm. Carbon concentration corresponding to thinness 2.00±0.01 mm of the second calibration curve was calculated as 0.08506 ppma. This value is different from the carbon concentration of FZ single crystal silicon separately produced from the same polycrystalline silicon rod only by 3%.

INDUSTRIAL APPLICABILITY

As explained above, according to the present invention, it is possible to perform approximate concentration measurement of substitutional carbon in polycrystalline silicon without applying single crystallization by the FZ method or the like and without performing special pre-heat treatment. That is, according to the present invention, there is provided a method for making it possible to easily and simply measure approximate concentration of substitutional carbon impurities in a desired position in a polycrystalline silicon rod.

REFERENCE SIGNS LIST

10 Core (Silicon block)
11 FZ single crystal rod near region of gripped portion
12, 13 Polycrystalline silicon plates
20 FZ single crystal rod
21 Cone portion
22 Disc-like FZ crystal
30 Seed

The invention claimed is:

1. A method for measuring carbon concentration in polycrystalline silicon comprising:
    slicing out a polycrystalline silicon plate from a polycrystalline silicon rod;
    mirror-polishing both surfaces of the polycrystalline silicon plate to reduce the polycrystalline silicon plate to thickness of 2.12±0.01 mm;
    creating a calibration curve according to an infrared absorption spectroscopy and on the basis of a standard measurement method using a single crystal silicon standard sample having known substitutional carbon concentration and thickness of 2.00±0.01 mm;
    calculating, under conditions same as conditions during the calibration curve creation, an infrared absorption spectrum in a frequency domain including an absorption zone peak of substitutional carbon in a desired place of the polycrystalline silicon plate after the mirror polishing; and
    calculating substitutional carbon concentration of the polycrystalline silicon plate on the basis of the calibration curve without performing thickness correction.

2. A method of measuring carbon concentration in polycrystalline silicon comprising:
    slicing out at least two adjacent polycrystalline silicon plates having different thicknesses from a polycrystalline silicon rod;
    mirror-polishing both surfaces of each of the polycrystalline silicon plates to prepare a first polycrystalline silicon plate thinner than 2.12 mm and a second polycrystalline silicon plate thicker than 2.12 mm;
    creating a first calibration curve according to an infrared absorption spectroscopy and on the basis of a standard measurement method using a single crystal silicon standard sample having known substitutional carbon concentration and thickness of 2.00±0.01 mm;
    calculating, under conditions same as conditions during the first calibration curve creation, an infrared absorption spectrum in a frequency domain including an absorption zone peak of substitutional carbon in a desired place of the first and second polycrystalline silicon plates after the mirror polishing;
    calculating substitutional carbon concentration of the first and second polycrystalline silicon plates on the basis of the first calibration curve without performing thickness correction;
    creating a second calibration curve from the substitutional carbon concentrations and the thicknesses of the first and second polycrystalline silicon plates; and setting carbon concentration corresponding to the thickness 2.00±0.01 mm of the second calibration curve as carbon concentration of a sliced-out region of the polycrystalline silicon plate.

\* \* \* \* \*